United States Patent
Porro

(10) Patent No.: US 11,576,959 B2
(45) Date of Patent: *Feb. 14, 2023

(54) GLYCOCONJUGATE VACCINES COMPRISING BASIC UNITS OF A MOLECULAR CONSTRUCT EXPRESSING BUILT-IN MULTIPLE EPITOPES FOR THE FORMULATION OF A BROAD-SPECTRUM VACCINE AGAINST INFECTIONS DUE TO ENTEROPATHOGENIC BACTERIA

(71) Applicant: BIOSYNTH S.R.L., Rapolano Terme (IT)

(72) Inventor: Massimo Porro, Rapolano Terme (IT)

(73) Assignee: BIOSYNTH S.R.L., Rapolano Terme (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/157,969

(22) Filed: Jan. 25, 2021

(65) Prior Publication Data

US 2021/0138059 A1 May 13, 2021

Related U.S. Application Data

(60) Division of application No. 16/666,367, filed on Oct. 28, 2019, now Pat. No. 11,246,919, which is a continuation of application No. 15/329,205, filed as application No. PCT/EP2015/066988 on Jul. 24, 2015, now Pat. No. 10,500,263.

(30) Foreign Application Priority Data

Jul. 25, 2014 (IT) .......................... MI2014A001361

(51) Int. Cl.
| | |
|---|---|
| *A61K 39/02* | (2006.01) |
| *A61K 47/64* | (2017.01) |
| *A61K 39/108* | (2006.01) |
| *A61K 39/112* | (2006.01) |
| *A61K 39/00* | (2006.01) |

(52) U.S. Cl.
CPC ........ *A61K 39/107* (2013.01); *A61K 39/0258* (2013.01); *A61K 39/0275* (2013.01); *A61K 47/646* (2017.08); *A61K 2039/54* (2013.01); *A61K 2039/545* (2013.01); *A61K 2039/55505* (2013.01); *A61K 2039/575* (2013.01); *A61K 2039/6037* (2013.01); *A61K 2039/627* (2013.01); *A61K 2039/70* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 5,919,463 | A  * | 7/1999  | Thomas, Jr. | C07K 14/33 424/234.1 |
| 6,951,652 | B2 * | 10/2005 | Porro | A61P 31/04 424/193.1 |
| 8,597,663 | B2 * | 12/2013 | Monteiro | C12P 19/04 424/234.1 |
| 8,921,529 | B2 * | 12/2014 | Shone | C07K 16/1282 530/389.5 |
| 9,238,669 | B2 * | 1/2016  | Seeberger | C07H 5/04 |
| 9,463,250 | B2 * | 10/2016 | Bigio | B01D 15/3847 |
| 9,585,921 | B2 * | 3/2017  | McKenzie | A61K 35/745 |
| 9,694,064 | B2 * | 7/2017  | Boutriau | A61P 37/04 |
| 9,745,354 | B2 * | 8/2017  | Ruppen | A61K 39/08 |
| 9,815,889 | B2 * | 11/2017 | Seeberger | C07K 16/1282 |
| 10,286,054 | B2 * | 5/2019 | Boedeker | A61P 31/06 |
| 10,300,135 | B2 * | 5/2019 | Porro | A61K 39/092 |
| 10,500,263 | B2 * | 12/2019 | Porro | A61K 39/107 |
| 10,588,857 | B2 * | 3/2020 | Schentag | A61P 31/04 |
| 10,668,142 | B2 * | 6/2020 | Costantino | A61P 31/00 |
| 11,147,872 | B2 * | 10/2021 | Porro | A61K 39/385 |
| 2002/0034520 | A1 * | 3/2002 | Porro | A61K 39/0275 424/234.1 |

(Continued)

FOREIGN PATENT DOCUMENTS

| | | | | |
|---|---|---|---|---|
| CA | 2954087 A1 * | 1/2016 | ........ | A61K 39/0258 |
| EP | 1501542 A1 * | 2/2005 | .......... | A61K 39/092 |

(Continued)

OTHER PUBLICATIONS

Anish et al, Chemistry and Biology, Jan. 16, 2014. 21:38-50 (Year: 2014).*

(Continued)

*Primary Examiner* — Nita M. Minnifield
(74) *Attorney, Agent, or Firm* — Hedman & Costigan, P.C.; James V. Costigan; Kathleen A. Costigan

(57) ABSTRACT

The present invention refers to new glycoconjugate antigens expressing built-in multiple epitopes and to polyvalent glycoconjugate vaccines intended for the protection of mammalians, and particularly for the protection of the human population from enteropathogenic bacteria, such as the Gram-positive anaerobic bacterium *Clostridium difficile* and the Gram-negative bacteria *Salmonella typhi*, *Escherichia Coli*, *Vibrio Cholerae*, *Shigella flexneri*, *Salmonella typhimurium*, *Salmonella enteritidis*, *Salmonella paratyphi* A, *Shigella sonnei*, *Shigella dysenteriae*, *Salmonella cholerasuis*, *Klebsiella*, *Enterobacter*, *Pseudomonas aeruginosa* and/or from viral gastrointestinal infections due to human noroviruses.

2 Claims, 1 Drawing Sheet

(56) References Cited

U.S. PATENT DOCUMENTS

| | | | |
|---|---|---|---|
| 2005/0202042 A1* | 9/2005 | Wilkins | A61P 31/12 424/203.1 |
| 2006/0165730 A1* | 7/2006 | Porro | A61K 39/095 530/395 |
| 2012/0020996 A1* | 1/2012 | Telfer | A61P 37/04 536/23.7 |
| 2014/0193416 A1* | 7/2014 | Seeberger | C07H 5/04 530/387.5 |
| 2015/0313984 A1* | 11/2015 | Boutriau | A61P 31/04 424/190.1 |
| 2016/0136285 A1* | 5/2016 | Gozdziewicz | A61K 39/0283 530/387.9 |
| 2016/0137724 A1* | 5/2016 | Seeberger | A61K 39/40 530/387.5 |
| 2016/0368972 A1* | 12/2016 | Shoemaker | C07K 16/1282 |
| 2017/0143821 A1* | 5/2017 | Porro | A61K 39/095 |
| 2017/0209563 A1* | 7/2017 | Porro | A61K 39/107 |
| 2019/0224309 A1* | 7/2019 | Porro | A61K 39/092 |
| 2019/0224310 A1* | 7/2019 | Porro | A61K 39/095 |
| 2019/0231869 A1* | 8/2019 | Hargis | A61K 39/08 |
| 2020/0129606 A1* | 4/2020 | Porro | A61P 31/04 |
| 2021/0138059 A1* | 5/2021 | Porro | A61K 39/107 |

FOREIGN PATENT DOCUMENTS

| | | | | |
|---|---|---|---|---|
| EP | 3003362 A1 * | 4/2016 | | A61K 39/025 |
| EP | 3174553 A1 * | 6/2017 | | A61K 39/0258 |
| WO | WO-2004052394 A1 * | 6/2004 | | A61K 39/102 |
| WO | WO-2004067030 A2 * | 8/2004 | | A61K 39/095 |
| WO | WO-2013017254 A1 * | 2/2013 | | A61K 31/713 |
| WO | WO-2014067582 A1 * | 5/2014 | | H04W 4/06 |
| WO | WO-2014086787 A1 * | 6/2014 | | A61K 39/08 |
| WO | WO-2014118201 A1 * | 8/2014 | | A61K 39/092 |
| WO | WO-2014195880 A1 * | 12/2014 | | A61K 39/025 |
| WO | WO-2016012587 A1 * | 1/2016 | | A61K 39/0258 |

OTHER PUBLICATIONS

Chan et al, Scientific Reports, 5:11507, DOI:10.103//srep11507, 8 pages, published: Jun. 17, 2015 (Year: 2015).*
Jones et al, Science, Nov. 7, 2014, 346/6210:755-759 (Year: 2014).*
Oberli et al, Chemistry and Biology, 18:580-588, May 27, 2011. published:May 26, 2011 (Year: 2011).*
Pavliakova et al, Infection and Immunity, Apr. 2000. 68/4:2161-2166 (Year: 2000).*
Sougioultzis et al, Gastroenterology, Mar. 2005,128:764-770 (Year: 2005).*
Yang et al, Bulletin of the World Health Organization. 2001,79/7:625-631 (Year: 2001).*
Donald et al, Microbiology, 2013, 159:1254-1266. (Year: 2013).*
Foglia et al, Vaccine, 2012, 30:4307-4309. (Year: 2012).*
Hegerie et al, PLoSONE 2018, 13/9:e0203143, 23 pages. published: Sep. 6, 2018 (Year: 2018).*
Napolitano et al, Surgery, Aug. 2017, 162:325-348 (Year: 2017).*
Barreau et al, Current Opinion in Microbiology, 2014, 17:91-98. available online: Jan. 14, 2014 (Year: 2014).*
Guzman et al, EcoSal Plus 2013; doi:10.1128/ecosalplus.8.8.14. (Year: 2013).*
Mani et al, Vaccine 34, 2016, pp. 2887-2894. available online: Mar. 12, 2016 (Year: 2016).*
Kirchin et al, Clinical Infectious Diseases. 2020 . 70(1):1-10. published online: May 24, 2019. (Year: 2020).*
MacLennan et al, Human Vaccines and Therapeutics, Jun. 2014, 10:6:1478-1493. (Year: 2014).*
Broecker et al, ACS Chem. Biol. 2019, 14:2720-2728. 2019. published: Nov. 6, 2019 (Year: 2019).*

\* cited by examiner

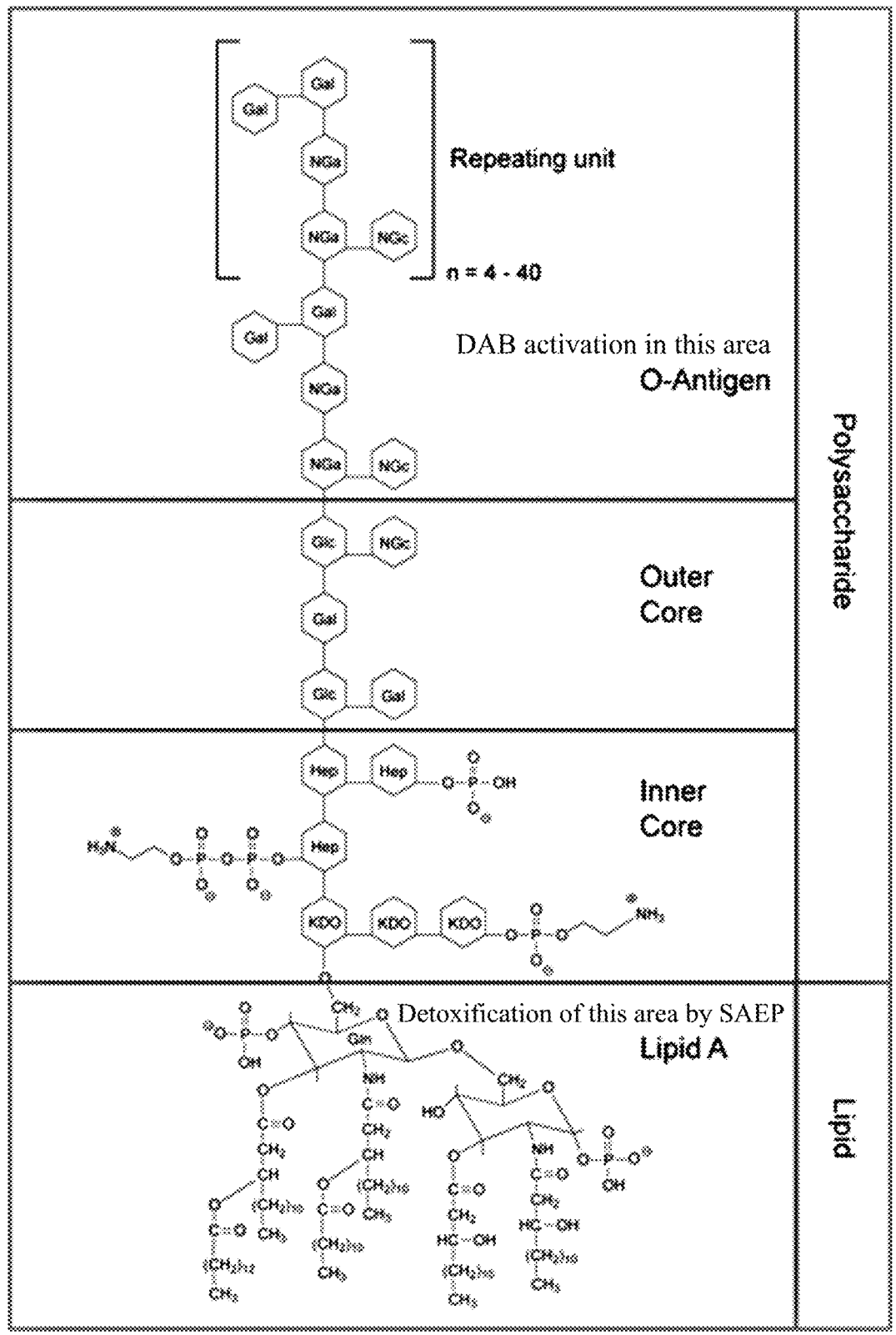

GLYCOCONJUGATE VACCINES COMPRISING BASIC UNITS OF A MOLECULAR CONSTRUCT EXPRESSING BUILT-IN MULTIPLE EPITOPES FOR THE FORMULATION OF A BROAD-SPECTRUM VACCINE AGAINST INFECTIONS DUE TO ENTEROPATHOGENIC BACTERIA

The present invention refers to new glycoconjugate antigens expressing built-in multiple epitopes and to polyvalent glycoconjugate vaccines intended for the protection of mammalians, and particularly for the protection of the human population from enteropathogenic bacteria, such as the Gram-positive anaerobic bacterium *Clostridium difficile* and the Gram-negative bacteria *Salmonella typhi, Escherichia Coli, Vibrio Cholerae, Shigella flexneri, Salmonella typhimurium, Salmonella enteritidis, Salmonella paratyphi* A, *Shigella sonnei, Shigella dysenteriae, Salmonella cholerasuis, Klebsiella, Enterobacter, Pseudomonas aeruginosa* and/or from viral gastrointestinal infections due to human noroviruses.

*Clostridium difficile* is a spore-forming Gram-positive *bacillus* producing two Exotoxins (Enterotoxin A and Cytotoxin B) which are pathogenic to humans.

*C. difficile* is the primary cause of antibiotic related infectious diarrhoea in elderly hospitalized patients in developed countries (Simor et al., 2002). Symptoms of *C. difficile* associated disease (CDAD) range from diarrhoea to severe colitis, toxic megacolon, sepsis and death. Over recent years, increases in disease incidence, severity and recurrence are largely due to the emergence of hypervirulent strains associated with epidemic hospital outbreaks combined with an increase in resistance to commonly used antibiotics (Rupnik et al., 2009).

A prophylactic vaccine capable of neutralizing the *C. difficile* Enterotoxin A and Cytotoxin B, the two Toxins of the pathogen, is reported to be as the candidate example of vaccine under industrial development (Donald R. et al., 2013).

Toxins A and B are very large proteins of 308 kDa and 270 kDa, respectively, that are structurally related, sharing homologous functional domains that mediate intracellular uptake and delivery of a cytotoxic glucosyltransferase.

Toxin A (Enterotoxin) is composed of 2,710 AA and displays in its sequence 223 Lys residues (8.22% cationicity); Toxin B (Cytotoxin) is composed of 2,366 AA and displays in its sequence 156 Lys residues (6.59% cationicity) (see for reference the website: http://www.uniprot.org/uniprot/P16154 and http://www.ncbi.nlm.nih.gov/protein/AGG91548.1). Although these two toxins differ individually in their potency and effects in "in vivo" models, past studies in animal models suggest that they both contribute to disease in natural infections (Lyerly et al., 1985). Furthermore, vaccination with both Toxin A and Toxin B—but not with either alone—conferred protection in a hamster model of infection (Libby J. M. et al., 1982).

Recognition of the ability of the humoral immune response to control CDAD prompted the successful use of passive immunotherapy with pooled human immunoglobulin containing anti-Toxin A and B antibodies to treat severe CDAD (Salcedo J. et al., 1997). Furthermore, reduction in recurrence of CDAD was achieved in a Phase I clinical trial with A and B anti-Toxin monoclonal antibodies in combination with standard antibiotic therapy (Lowy I. et al., 2010).

In addition, in a small study with three patients with chronic relapsing CDAD, an investigational vaccine using formalin-inactivated A and B Toxoid antigens prevented CDAD recurrence (Sougioultzis S. et al., 2005).

Collectively, these observations provide validation for, and encourage further development of *C. difficile* Toxin A-based and Toxin B-based vaccines to prevent CDAD. As above recalled, there are now two candidate vaccines in clinical trials, which are based on the two recombinant/formalin-treated Toxoid proteins A and B.

Strategies for developing vaccines based on single specificities for *C. difficile* Toxoids (either detoxified by formalin treatment or by DNA recombinant technology) are well documented, as above recalled. Also well documented are the studies for using *C. difficile* recombinant enterotoxin A (rARU) as carrier protein for each of the capsular Ps of Silexneri type 2a, *E. coli* K1 and Pneumococcus type 14 (Pavliakova D. et al., 2000) prepared as single conjugates. Clearly, the simultaneous administration of the single three conjugates inevitably results in an overload for the immune system of the host due to the total, other than heterogeneous, amount of injected carrier protein, namely the recombinant repeating unit of *Clostridium difficile* enterotoxin A (respectively 1.29 µg, 3.9 µg and 8.08 µg of rARU for each conjugate Pn14-rARU, SF-rARU and K1-rARU).

Very recently, structural parts of the two Toxins have been used as non-toxic carriers for the Ps II antigen of *C. difficile* (Romano M. et al, 2014). Although *C. difficile* also produces three different capsular Ps, evidence is pointing in the direction of the two Toxins as target for efficaciously fighting the pathology, as in the historical cases of Diphtheria and Tetanus infections.

None of these previous works, however, have reported on the possibility to prepare a broad-spectrum enteric vaccine for inducing immunity against several carbohydrate antigens from antibiotic-resistant enteropathogenic bacteria (multiple-specificities) in a human host, particularly in a child, while using the minimum amount of carrier proteins for reducing the antigenic burden of the vaccine(s) on the host immune system, whilst maintaining the specific immunogenic activity and in vivo protection qualitatively achievable by administering monovalent conjugates. However, animal models do not allow to draw conclusions on the quantitative aspects of the induced antibody titers by the multiple antigens of the invention, in comparison to the monovalent ones, since it is well known to the experts in the Field that only human infants can reliably discriminate among the eventually different helper T-dependent activity of different models of conjugate entities.

The author of the present invention has now obtained multiple-epitope molecular constructs as basic unit for the preparation of a multiple-epitopes glycoconjugate vaccine to be used as broad-spectrum enteric vaccine for the protection of the human population from enteropathogenic bacteria. In fact, the author of the present invention focuses on the urgent problem nowadays reported for several intestinal pathogens which have become antibiotic resistant: the Gram-positive anaerobic bacterium *Clostridium difficile* and the Gram-negative bacteria *Salmonella typhi, Escherichia Coli, Vibrio Cholerae, Shigella flexneri, Salmonella typhimurium, Salmonella enteritidis, Salmonella paratyphi* A, *Shigella sonnei Shigella dysenteriae, Salmonella cholerasuis, Klebsiella, Enterobacter, Pseudomonas aeruginosa*. Because of their increasing antibiotic resistance, intestinal infections due to this panel of bacteria may often lead to sepsis with consequent death of the host.

Therefore, it is an object of the present invention an antigenic multivalent molecular construct consisting of basic units comprising the helper-T dependent carrier detoxified proteins selected between Enterotoxoid A and Cytotoxoid B from *Clostridium difficile* covalently bound to a minimum of three carbohydrate structures from enteropathogenic bacteria selected between bacterial polysaccharides or detoxified lipopolysaccharides (such as SAEP-detoxified LPS or Endotoxoids) of different serological specificity, wherein each carbohydrate structure comprises at least one of the repeating basic epitopes consisting of a minimum of five to twelve monosaccharide residues (preferably a minimum of eight to twelve monosaccharide residues), wherein at least one mole of carrier protein is covalently bound to at least one mole of type-specific or group-specific carbohydrate structures, or to the total amount of carbohydrate structures being considered as the sum of the at least three type-specific or group-specific carbohydrates. Preferably, said saccharide residues are assessed by molecular mass determination and NMR spectroscopy, said repeating basic epitopes being antigenically assessed by reactivity with type-specific or group-specific polyclonal or monoclonal antibodies through the determination of their respective MIC50 values in the inhibition of their homologous Polysaccharide-Antibody reference system.

Enteropathogenic bacteria according to the present invention are those intestinal pathogens which have become antibiotic resistant such as: the Gram-positive anaerobic bacterium *Clostridium difficile* and the Gram-negative bacteria *Salmonella typhi, Escherichia Coli, Vibrio Cholerae, Shigella flexneri, Salmonella typhimurium, Salmonella enteritidis, Salmonella paratyphi* A, *Shigella sonnei, Shigella dysenteriae, Salmonella cholerasuis, Klebsiella, Enterobacter, Pseudomonas aeruginosa*.

The Figure depicts a scheme that represents the general LPS structure of Enterobacteriaceae with located sites of DAB-activation.

According to a preferred embodiment of the present invention the toxoid proteins Enterotoxoid A and Cytotoxoid B from *Clostridium difficile* are detoxified by chemical method, such as formalin-treatment, like historically known for diphtheria and tetanus toxoids, or by DNA recombinant technology.

In the molecular constructs according to the present invention each of the two toxoid proteins may support a minimum of three polysaccharides of different antigenicity (such as oligosaccharides or polysaccharides deriving from bacterial capsular polysaccharides) or a minimum of three detoxified lipopolysaccharides (or LPS, Endotoxin) of different antigenicity. The molecular constructs obtained in this way with LPS, however, result to be toxic because the Lipid A moiety of LPS is actively present in the molecular structure and can activate, via interaction with the CD14 and TLR4-like receptors, the pro-inflammatory cytokine cascade typical of LPS. In order to pursue and achieve the safe use of the Toxoid-LPS conjugate entity, the LPS structure must therefore undergo detoxification.

This can be achieved by:
1) cleaving out the Lipid A moiety, or
2) by saturation of the Lipid A-binding site through a specific strategy that use the Synthetic Anti-Endotoxin Peptides (SAEP) in order to obtain Endotoxoids (alternatively named SAEP-detoxified LPS, SAEP-detoxified endotoxin) which conserve their complete supra-molecular antigenic repertoire in the form of micelle-like structures (WO 2004/052394 A1).

The latter detoxification process is the preferred embodiment in the context of the present invention. Specifically, an Endotoxoid, originating from a given species-specific (immunotype) Endotoxin (Lipopolysaccharide) is prepared according to the scientific concept reported by Rustici et al. (Science 259: 361-365, 1993) and in the previously disclosed molecular details reported in the U.S. Pat. No. 6,951,652 and in the U.S. Pat. No. 7,507,718.

Therefore, an Endotoxoid is a molecular entity composed of an equimolar complex of SAEP, Synthetic Anti Endotoxin Peptides, and LPS (Endotoxin), which, in the form of a multiple-epitope conjugate with a *C. difficile* Toxoid (A or B) satisfies the chemical equation:

$$\text{Toxoid-(LPS)}_3 + 3\ \text{SAEP} \rightarrow \text{Toxoid-(Endotoxoid)}_3$$

(see also below Example 3).

According to preferred embodiment of the molecular constructs of the present invention, capsular polysaccharide antigens may be selected between the group comprising *Escherichia coli* K types (1, 2, 5, 12, 13), *Salmonella typhi* (Vi antigen), *Vibrio cholerae* 0139 and *Clostridium difficile*.

*Clostridium difficile*, as a Gram-positive bacterium, also features a carbohydrate capsule involving at least three different Ps structures (PsI, PsII and PsIII).

According to an alternative embodiment of the molecular construct of the present invention, the two toxoid proteins serve as helper T-dependent carriers for glycoconjugates of the detoxified lipopolysaccharides (preferably SAEP-detoxified LPS or Endotoxoid) specific for *Shigella flexneri* 2a, *Vibrio cholerae* 01, *Salmonella cholerasuis, Escherichia coli* 0157/101/111, *Salmonella typhimurium, Salmonella enteritidis, Salmonella paratyphi* A, *Shigella sonnei, Shigella dysenteriae* type 1 and *Salmonella cholerasuis*.

The molecular constructs according to the invention induce serological specificity to the two carrier proteins (Enterotoxoid A and Cytotoxoid B of *C. difficile*) and to each of the at least three carried carbohydrate structures (briefly denominated either Ps or LPS/Endotoxoid) bound to each of the two carrier proteins, so that the relative specific antibodies exhibit neutralizing activity for the homologous natural toxins (Enterotoxin A and Cytotoxin B) of *Clostridium difficile* as well as bactericidal activity for *Salmonella typhi, Escherichia coli, Vibrio cholera, Salmonella enteritidis, Salmonella paratyphi* A, *Shigella dysenteriae* (other preferred carbohydrate antigens are from *Shigella flexneri, Salmonella typhimurium, Salmonella cholerasuis, Shigella sonnei* and from *C. difficile* itself).

According to the above, and as a non limiting series of examples, the author has prepared the following molecular constructs:

Enterotoxoid A covalently bound to the Ps of *S. typhi* (Vi), *V. cholerae* (0139) and *E. coli* (K1);
Cytotoxoid B covalently bound to the same three Ps of *S. typhi* (Vi), *V. cholerae* (0139) and *E. coli* (K1);
Enterotoxoid A covalently bound to the LPS/Endotoxoids of *S. enteritidis, S. paratyphi* A and *S. dysenteriae*;
Cytotoxoid B covalently bound to the same three LPS/Endotoxoids of *S. enteritidis, S. paratyphi* A and *S. dysenteriae*.

The invention further relates to the above antigenic multivalent molecular construct for use in a vaccine for the protection of a subject from the infections due to at least one enteropathogenic bacteria selected from *Clostridium difficile, Salmonella typhi, Escherichia coli, Vibrio cholerae, Salmonella enteritidis, Shigella flexneri, Salmonella paratyphi* A, *Salmonella dysenteriae, Salmonella cholerasuis* or a combination thereof.

In a preferred embodiment either a single or a combination of different antigenic multivalent molecular constructs may be used for the preparation of the vaccine.

It is a further object of the present invention a vaccine formulation comprising at least one antigenic multivalent molecular construct as above in a physiologically acceptable vehicle, optionally together with an adjuvant or excipients pharmaceutically acceptable.

The antigenic molecular constructs may have an homogeneous or mixed pattern of carrier antigen and carried antigens. The term carrier antigen refers to the toxoid proteins Enterotoxoid A or Cytotoxoid B from *C. difficile*; the term carried antigens refers to the carbohydrate structures (briefly denominated either capsular Ps or LPS/Endotoxoid) bound to each of the two carrier proteins. The term homogeneous or mixed refer to the source of the carried antigens in respect to the carrier antigen (i.e. all the carrier and carried antigens originate from *C. difficile;* the carried antigens originate from the same or different intestinal pathogens).

According to a preferred embodiment of the vaccine formulation of the invention, the dose of each carrier antigen and/or carried antigens ranges between 0.1 to 100 µg, preferably being 1-10 µg.

Preferably, said vaccine formulations further comprises a mineral or a chemically synthetic or a biological adjuvant. Mineral or chemically synthetic or biological adjuvants can be used with the molecular construct disclosed in this application, in order to benefit from any immunological boost that can be effective in lowering the optimal immunogenic dose in humans so to further reduce the total amount of carrier protein. Particularly, preferred inorganic adjuvants in the vaccine formulations according to the invention for use in human beings are selected between Aluminium Phosphate ($AlPO_4$) and Aluminium Hydroxide; preferred organic adjuvants are selected from squalene-based adjuvants such as MF59, QF 21, Addavax; preferred biological antigens are selected between the bacterial antigens monophosphoryl-lipid A, trehalose dicorynomycolate (Ribi's adjuvant).

In vaccine formulations for use in the veterinary field Freund's adjuvant (complete or incomplete) is preferred. The dose of adjuvant may range between 0.1-1 mg/dose, preferably being 0.5 mg/dose.

More preferably, such formulation is suitable for the administration by subcutaneous or intramuscular or intradermal or transcutaneous route. Conveniently, such administration may be carried out by conventional syringe injection or needle-free tools.

The vaccine formulations according to the invention may be administered according to a protocol which requires single or multiple administrations, according to the physician, pediatrician or veterinary instructions.

The invention further relates to a broad-spectrum polyvalent vaccine formulation as above defined for use in medical human or veterinary field for the protection of a subject from the infections due to at least one enterobacterial pathogens selected among *Clostridium difficile, Salmonella typhi, Escherichia coli, Vibrio cholerae, Salmonella enteritidis, Shigella flexneri, Salmonella paratyphi* A, *Salmonella dysenteriae, Salmonella cholerasuis* or a combination thereof. Preferably, said subject to be treated belongs to the paediatric and to the elderly population.

The actual formulation of such vaccine (e.g.: the species-specificity of the Gram-negative enteric bacteria from which Ps and LPS derive) may depend from the regional epidemiology so that each triad of antigenic conjugates, although using always one or both of the two carrier proteins Enterotoxoid A and Cytotoxoid B from *C. difficile*, purposely will carry specific Ps or LPS/Endotoxoid antigens according to the selected regional epidemiology.

In a particular embodiment of the present invention the vaccine formulation comprises at least two different antigenic molecular constructs wherein each of the two proteins Enterotoxoid A and Cytotoxoid B from *C. difficile* may serve as carrier protein for the three polysaccharides (PsI, PsII and PsIII) of *C. difficile* so that the two combined triads of conjugated antigens will represent a specific vaccine limited to the infections of *C. difficile* where the antitoxic activity induced by the two protein toxoids may be paralleled by the local and systemic anti-capsular activity resulting in the clearance of the bacterium by the host immune system.

Such single-triad molecular constructs have been also formulated as combined multi-valent compositions containing both kind of antigenic molecular models for achieving the broadest antigenic spectrum such as:

Enterotoxoid A covalently bound to the Ps of *S. typhi* (Vi), *V. cholerae* (O139) and *E. coli* (K1) combined with Cytotoxoid B covalently bound to the same three Ps antigens;

Enterotoxoid A or Cytotoxoid B covalently bound to the Ps of *S. typhi* (Vi), *V. cholerae* (O139) and *E. coli* (K1) combined with Cytotoxoid B or Enterotoxoid A covalently bound to the three Endotoxoid antigens of *S. enteritidis, S. paratyphi* A and *S. dysenteriae*.

It has been recently reported on the experimental evidence that human and mouse noroviruses infect B cells in vitro, and likely in vivo, through the involvement of enteric bacteria working as a stimulatory factor for norovirus infection. This biological synergism has been suggested to be at the basis of the mechanism by which noroviruses may become infective and develop epidemic and sporadic gastroenteritis in humans (Jones M. K. et al., Science, 346: 755-759, 2014).

In line with these observations, murine hosts undergoing antibiotic treatment for depleting the intestinal microbiota, have shown a significant reduction of mouse norovirus replication in the experiments reported by the authors.

From this evidence, the author of the present Application derived the principle of targeting the continuously expanding world of antibiotic-resistant enteropathogenic bacteria with the vaccine compositions herein disclosed in order to possibly limit, in parallel to enteric bacterial infections, the replication of noroviruses responsible for acute gastroenteritis.

Norovirus gastroenteritis is a widespread and potentially severe illness characterized by the acute onset of nausea, vomiting, abdominal cramps, diarrhea and occasionally fever. Noroviruses are highly infective and easily transmitted from person to person or via contaminated environments. Epidemic outbreaks occur in community environments, particularly hospitals, hotels, schools, day care facilities and nursing homes, with mounting socioeconomic cost to families, the health care system and businesses. Military units are significantly affected when the virus strikes, as outbreaks impact combat readiness. Severe clinical outcomes are reported in older adults, children and immunocompromised individuals in whom infection can lead to substantial complications and can even lead to death. It is estimated that, worldwide, noroviruses cause one in five cases of viral gastroenteritis. An estimated annual 300 million cases of norovirus infection contribute to roughly 260,000 deaths, mostly in low-income countries. Noroviruses are classified in at least 5 genogroups and in at least 40 genotypes; their distribution in selected geographic areas has been recently evaluated in children and elders, with an incidence of 1,475 cases/100,000 persons-year in young children (≤5 ys.) and 585 cases/100,000 persons-year in elders (≥65 ys.)(Chan M. et al, Scientific Reports, 2015). Over time, noroviruses evade natural immunity by antigenic drift, which allows them to escape from antibodies produced in response to earlier infections.

It is therefore another aspect of the present invention the provision of broad-spectrum polyvalent vaccine formulation for use in the prevention and/or treatment of enteropathogenic bacteria which then may target, in parallel, viral gastrointestinal infections due to human noroviruses.

Recent efforts to develop a norovirus vaccine have focused on virus-like particles (VLPs), which are constructed from molecules of the virus's capsid (outer shell). In a phase I clinical trial, one multivalent VLP vaccine elicited antibody generation, but did not confer immunity to the tested strain of virus. However, in a more recent study, Lindesmith and colleagues (2015) characterized serum specimens from ten multivalent VLP vaccine clinical trial participants for antibodies to vaccine VLPs and also to VLPs representing viruses that were not contained in the vaccine. The researchers found that VLP vaccine can rapidly elicit antibody responses to a broad range of vaccine and non-vaccine VLPs, including to two VLPs representing human noroviruses that they could not have previously encountered. Overall, antibodies to norovirus strains to which participants had previously been exposed, dominated the immune response. These findings may encourage the development of a norovirus-based vaccine assuming that this approach may overcome the ability of noroviruses to evade immunity by antigenic drift. In any event, this would be a strategy directed to eventually contain the virus during the phase of the infection in which the virus particles are spreading out of the bacterial cells hosting it, rather than to block the virus replication at the base, once it is still inside the enteropathogenic bacteria which are shielding it, as the author of the present Application is proposing by the use of a broad-spectrum vaccine targeting enteropathogenic bacteria. Eventually, the concomitant and/or parallel use of these two strategies (e.g.: the use of the two vaccines targeting the norovirus as well as its bacterial host) could constitute a powerful tool for achieving a broad-spectrum anti-viral protection for the human host.

The present invention further relates to a conjugation process for preparing the antigenic multivalent molecular construct according to the invention (which employs the same chemistry disclosed in the patent EP 1501542), wherein each of the at least three carbohydrate structures selected among:

capsular polysaccharides of *Salmonella typhi*, *Vibrio cholerae*, *Clostridium difficile* and *Escherichia coli* or lipopolysaccharides from *Clostridium difficile*, *Salmonella typhi*, *Escherichia coli*, *Vibrio cholerae*, *Salmonella enteritidis*, *Shigella flexneri*, *Salmonella paratyphi* A, *Salmonella dysenteriae*, *Salmonella cholerasuis* is chemically activated to mono-functionality or polyfunctionality by O-de-hydrogen uncoupling via oxidation and reductive amination forming imine reduced bonds with an alkyl diamine spacer, then derivatized to active esters, such ester-derivative carbohydrate structures being finally and simultaneously coupled to the amino groups of the polyfunctional carrier protein Cytotoxoid B or Enterotoxoid A from *C. difficile* through the formation of amide bonds;

wherein at least one mole of carrier protein is reacted with at least one mole of carbohydrate structures, considering such a total amount as the one composed by the molar sum of each of the at least three type-specific or group-specific carbohydrate structures. Preferably, said carbohydrate structures are chemically activated in their corresponding diamine butyric acid derivatives and the active esters are succinimidyl esters.

As an example, the chemical activation of the triad of polysaccharide from the capsule of *S. typhi*, *E. coli* and *V. cholerae* to their homologous Ps-DAB (diamine butyric acid derivative) has been performed according to the process disclosed by the Applicant in Claim 1 of EP 1501542, while the polyfunctional carrier proteins were the Enterotoxoid A and Cytotoxoid B from *C. difficile*.

Alternatively, the conjugation process for preparing the antigenic multivalent molecular constructs of the invention employs the chemistry disclosed in Claim 8 of EP 1501542 involving simultaneous coupling (or step-by-step coupling) of the amino groups of the poly-functional carrier proteins Cytotoxoid B or Enterotoxoid A from *C. difficile* with the at least three different carbohydrate structures selected between capsular polysaccharides of *Salmonella typhi*, *Vibrio cholerae*, *Clostridium difficile* and *Escherichia coli* or lipopolysaccharides from *Salmonella typhi*, *Escherichia coli*, *Vibrio cholerae*, *Salmonella enteritidis*, *Shigella flexneri*, *Salmonella paratyphi* A, *Salmonella dysenteriae*, *Salmonella cholerasuis* via reductive amination forming imine-reduced bond, such carbohydrate structures being previously activated to monofunctionality or polyfunctionality, with or without spacers, by O-de-hydrogen uncoupling via oxidation;

wherein at least one mole of carrier protein is reacted with at least one mole of carbohydrate structures, considering such a total amount as the one composed by the molar sum of each of the at least three type-specific or group-specific carbohydrate structures.

According to the present invention the term mole referred to both the carrier protein and the specific carbohydrate antigens encompasses the general measure unit (a mole) or a fraction of it (i.e. micromole or nanomole or picomole, all representative for a fraction of it).

When the conjugation process according to the invention contemplate lipopolysaccharides, these should be detoxified. Therefore, the conjugation process further comprises an additional step of detoxification of said lipopolysaccharides alternatively by a) cleaving out the Lipid A moiety before or after the coupling reaction is performed, or b) saturation of the Lipid A-binding site through a specific strategy that use the Synthetic Anti-Endotoxin Peptides (SAEP, like the SAEP2 see Rustici et al., Science 259: 361-365, 1993) before or after the coupling reaction is performed.

Preferably, such detoxified lipopolysaccharides are obtained through the latter procedure disclosed by the same author in the U.S. Pat. No. 6,951,652 (see page 16 and Claim 1) and U.S. Pat. No. 7,507,718 (see pages 33-34 and Claim 17) in order to obtain the corresponding Endotoxoids retaining the optimal antigenic features of the supramolecular, micelle-like, LPS structure(s) for the optimal expression of the relative immunogenic properties.

In addition to the above methods of detoxification, other methods may be used for the purpose and, among others, one may consider LPS detoxification by genetic engineering through the modification of the enzymatic path leading to the synthesis of Lipid A as well as detoxification by enzymatic or chemical hydrolysis of the ester-linked fatty acid chains present in the Lipid A structure.

Furthermore, in a preferred embodiment of the conjugation process of the invention, the carbohydrate structures of step a) comprise at least one of the repeating basic epitopes consisting of a minimum of five to twelve monosaccharide residues as assessed by molecular mass determination and NMR spectroscopy, said repeating basic epitopes being antigenically assessed by reactivity with type-specific or group-specific polyclonal or monoclonal antibodies through the determination of their respective MIC50 values in the inhibition of their homologous Polysaccharide-Antibody reference system.

It represents a final object of the present invention an antigenic multivalent molecular construct obtainable by the conjugation process above outlined.

As it can be inferred, the above disclosed molecular model can be further developed to contain more than three (for example four or five) different carbohydrate structures per single mole (or fractions of it) of protein carrier, this possibility depending from three main parameters of the molecular construct:

a) the physical-chemical features of the carrier protein, which structure should feature the highest possible amount of Lysine residues (source of reactive —$NH_2$ groups);

b) the "ad hoc" selected polydisperse MW of the different carbohydrate structures featuring an optimal activation rate while limiting the negative effects of steric hindrance phenomena in the coupling reaction, and c) the efficiency of the chemistry used for the activation of the different carbohydrate structures and for the synthesis of the molecular construct (the preferred chemistry for a high efficiency in the optimal activation of carbohydrate structures is the O-de-hydrogen uncoupling via oxidation, with or without spacer, while that for a high efficiency in the conjugation reaction is through amide bond formation via active esters between the carbohydrate structures and the carrier protein; also preferred for the conjugation reaction, is the chemistry which uses the formation of an imine reduced bond between the O-de-hydrogen uncoupling oxidized carbohydrate structures, with or without spacers, and the carrier protein, via direct reductive amination).

The process of conjugation employed according to the invention foresees the multi-step activation of the (at least three) Ps or LPS (that consequently may have indifferently, although homogeneously, either low or high MW) in order to optimize the coupling yields with the carrier protein.

The stoichiometric features of the present molecular constructs (w/w ratio Protein/Ps or Protein/LPS), which are in turn related to the immunizing dose of the molecular constructs have been carried out by the immunochemical method disclosed in the international patent application No. PCT/EP2014/051670.

This has allowed the possibility in the present invention to determine the quantitative amount of Ps or LPS even when having very similar structures if present in the same molecular construct. Finally, the present invention is directed to limit the amount of carrier protein in the vaccine formulation to the minimum immunogenically possible as related to the broader antigenic repertoire of the conjugate antigens, in order to contain the antigenic burden on the host's immune system for the molecular constructs obtainable through the conjugation processes above disclosed. This strategy is coherent with the containment of the clinical phenomenon today known as "carrier-specific immune interference" which is related to the amount of carrier protein used in a given glycoconjugate vaccine composition when considering the context of other vaccines administered during the immunization path of the mammalian host (Dagan R. et al, 2010; Lee L. H. and Blake M. S., 2012).

In the following experimental section the invention will be disclosed in more detail according to preferred embodiments. Such embodiments should be considered not limitative for the scope of protection of the present patent disclosure, but merely for illustrative purpose.

EXAMPLES

Example 1 i) Synthesis of the Tetravalent Conjugate Antigen Comprising Polysaccharides of S. typhi(Vi), E. coli (K1) and V. cholerae (0139) with the carrier protein Enterotoxoid A;

ii) Synthesis of the Tetravalent Conjugate Antigen Comprising Polysaccharides of *S. typhi* (Vi), *E. coli* (K1) and *V. cholerae* (0139) with the Carrier Protein Cytotoxoid B.

Chemical Activation of the Three Ps to the Homologous Ps-DAB (Diamine Butyric Acid Derivative)

This step has been performed according to the process disclosed by the Applicant in the Claim 1 (step A1) of the above mentioned patent EP1501542. Specific controls of such activation as well as the obtained characteristics of the activate Ps structures has been performed using $^1$H-NMR spectroscopy as reported in the international application No. PCT/EP2014/051670.

$^1$H-NMR Analysis of Ps-DAB Derivatives

1. Solution of Ps and Ps-DAB Derivatives for NMR Analysis 3-4 mg of polysaccharide sample (PS) or PS-DAB is solved in 0.7 ml of $D_2O$-phosphate buffer and transferred into a 5 mm NMR tube. The concentration of phosphate buffer prepared in $D_2O$ is 100 mM, pH=7. Trimethylsilylpropionic acid sodium salt (TSPA), $(CH_3)_3Si(CD_2)_2COONa$ is used as an internal reference. The concentration of TSPA is 1 mM.

2. NMR Equipment

High field NMR spectrometer (600 MHz) is used. A high resolution 5 mm probehead with z-gradient coil capable of producing gradients in the z-direction (parallel to the magnetic field) with a strength of at least 55 G. $cm^{-1}$ is employed.

3. Setup of NMR Experiments

After the introduction of the sample inside the magnet all the routine procedures have been carried out: tuning and matching, shimming, 90 degree pulse calibration. Presaturation can be used to suppress the residual HDO signal. For good presaturation the centre of the spectrum (O1) must be set exactly on the HDO signal (about 4.80 ppm), and good shimming is desirable as well.

After adjustment of parameters for presaturation, the parameters of diffusion gradient experiments are checked. The stimulated echo pulse sequence using bipolar gradients with a longitudinal eddy current delay is used.

4. Fingerprinting of DAB-Activation

Group —$CH_2$—$NH_2$ at 3.08 ppm

Group —$CH_2$—NH—$CH_2$— at 3.17 ppm

5. % of DAB Activation on Ps

% of DAB activation is in the range value of 0.5-5.0% moles DAB/moles BRU (Basic Repeating Unit of the Group-specific Ps) with an optimal molar range 1.5-3.0%.

Derivatization of Ps Vi, Ps 0139, Ps K1 to their Homologous Active Esters as Ps-DAB-MSE Derivatives This step has been performed according to the process disclosed by the applicant in Claim 8 of the European Patent EP 1501542, herewith included as a reference.

Simultaneous Coupling of the Three Activated (Poly-Functional) Ps to the (Poly-Functional) Carrier Protein Enterotoxoid A or Cytotoxoid B The chemical synthesis of the conjugate, also known as coupling reaction, has been performed according to the process disclosed by the applicant in Claim 8 of the European Patent EP1501542. The procedure, however, can be here considered as innovative because the three coupling reactions are simultaneously run, rather than proceeding in one coupling reaction at the time (or step-by-step process).

This procedure may be preferred to the step-by-step coupling of each Ps-activated antigen for the simple reason of shorting the reaction time, therefore improving the efficiency of the reaction, provided that the three activated-Ps are in the condition to comparatively compete at the equilibrium for the coupling reaction (this feature include comparable average MW, comparable range of Ps-DAB activation and comparable stoichiometric ratios among the reacting groups of the protein and those of the activated Ps).

The appropriate stoichiometry of reaction keeps in consideration the total amount of succinimidyl esters relative to the three Ps antigens activated and the amino groups of the carrier protein available. Stoichiometry is preferentially set as to consider the reactivity of no more than 20-25% of the amino groups available in the structure of Enterotoxoid A or Cytotoxoid B (as an example) in order for the protein to optimally conserve its antigenic repertoire.

The coupling reaction of Enterotoxoid A or Cytotoxoid B (briefly indicated as Toxoid) with Ps-DAB derivatives (Ps-DAB) is consistent with the following stoichiometry:

$$\text{Toxoid+4 Ps-DAB(MSE)} \rightarrow \text{Toxoid-(Ps)}_3\text{+Ps-DAB(MSE)}$$

Where the entity Ps-DAB(MSE) derivatives refer to the total of equal parts of each of the three type-specific Ps structures in reaction yielding a conjugate averaging 1 mole of protein for the total of 3 moles of type-specific Ps carried, plus the due excess of Ps-DAB(MSE) derivatives, as ruled by the equilibrium constant:

$$Keq = \frac{[Toxoid\text{-}(Ps)_3][Ps\text{-}DAB(MSE)]}{[Toxoid][Ps\text{-}DAB(MSE)]^4} = \frac{[Toxoid\text{-}(Ps)_3]}{[Toxoid][Ps\text{-}DAB(MSE)]^3}$$

The equation refers to the concentration of the total active esters (MSE) deriving from the sum of equal parts of the DAB-activated Ps antigens, which are in turn comparable to the amount of the DAB linker quantitated by $^1$H-NMR spectrometry which is present in each activated Ps antigen (conversion rate of Ps-DAB to Ps-DAB(MSE) ≥98% on molar basis).

The chemical equation makes evidence for the complete glycosylation of the Toxoid carrier protein. The equation also shows that the conjugation reaction depends from the concentrations of both reagents, the nucleophile (Toxoid through the epsilon-$NH_2$ groups of its Lys residues) and the electrophile (the carbonyl moiety of the ester groups of Ps derivatives) therefore being defined as $S_N2$ reaction.

The above considerations are consistent with the experimental observation that the highest yield in the glycosylation reaction obtained with Toxoid as carrier protein has been 100% of the carrier protein and about 80% (w/w) of the Ps-DAB-derivatives present in reaction, with the remaining part of them being a low amount of uncoupled Ps-derivatives necessary for pushing to the right side the equilibrium.

In this type of reactions, the solvent affects the rate of reaction because solvents may or may not surround the nucleophile, thus hindering or not hindering its approach to the carbon atom. Polar aprotic solvents, are generally better solvents for this reaction than polar protic solvents because polar protic solvents will be solvated by the solvent's hydrogen bonding for the nucleophile and thus hindering it from attacking the carbon with the leaving group. A polar aprotic solvent with low dielectric constant or a hindered dipole end, will favor $S_N2$ manner of nucleophylic substitution reaction (preferred examples are: DMSO, DMF, tetrahydrofuran etc.).

The temperature of reaction, which affects $K_{eq}$, is the lowest compatible with the use of the solvent chosen, when considering that the reaction is a spontaneous one (therefore being exothermic) and therefore is generally set between a temperature of 4° and 20° C.

In addition to the conjugation chemistry above detailed, other chemistries can be used to achieve the synthesis of the multivalent conjugate antigen; among these, the direct coupling of the protein (via reductive amination) to the oxidized Ps (via O-de-hydrogen uncoupling) or the use of heterologous and chemically complementary linkers that may serve to activate the Ps and the protein.

Also, in addition to the strategy of using chemistries leading to obtain multivalent cross-linked protein-Ps conjugates via the poly-functionality of the protein and that of the Ps components, one may consider the synthesis of the presently disclosed antigenic multivalent molecular construct as based on oligosaccharides derived from capsular Ps or from Lipid A-deprived oligosaccharides of LPS, activated at their end-reducing group for then being coupled to the carrier protein, as the applicant showed in another model of conjugate antigen in the above mentioned paper Porro M. et al. in Molecular Immunology, 23: 385-391, 1986.

Finally, the disclosed molecular construct might be thought to be prepared by enzymatic glycosylation in bacterial or yeast cells or other engineered living cells, using "ad hoc" DNA-recombinant techniques.

Example 2 iii) Synthesis of the Tetravalent Conjugate Antigen Comprising LPS (Lipopolysaccharides) of *S. enteritidis, S. paratyphi* A and *S. dysenteriae* with the Carrier Protein Cytotoxoid B;

iv) Synthesis of the Tetravalent Conjugate Antigen Comprising LPS (Lipopolysaccharides) of *S. enteritidis, S. paratyphi* A and *S. dysenteriae* with the Carrier Protein Enterotoxoid A.

Chemical Activation of the Three LPS to the Homologous LPS-DAB Derivatives (Diamine Butyric Acid Derivative)

The three LPS, were chemically derivatized in their O-antigen carbohydrate moiety to the corresponding -DAB derivatives (see the below scheme showing the DAB-activated area within the O-antigen carbohydrate moiety which is the most hydrophilic part of the LPS molecule). The "core" structure is difficult to be activated because is very close to the hydrophobic area (Lipid A), which is a quite kriptic structure responsible for the micelle-like structure of LPS, which is also responsible for the biological toxicity of LPS (e.g. local and systemic inflammation, TNF- and IL6-mediated, followed by pyrogenicity) as well as for the optimal expression of antigenicity and immunogenicity. In a preferred embodiment of the present Application, the biological toxicity of LPS is then selectively blocked through the high affinity binding with SAEP, which preserves such optimal features of LPS linked to its supramolecular, micelle-like, structure.

The step of DAB-activation has been performed according to the process disclosed by the Applicant in the Claim 1

(step A1) of the above mentioned patent EP1501542. Specific controls of such activation as well as the obtained characteristics of the activate Ps structures has been performed using $^1$H-NMR spectroscopy as reported in the international patent application No. PCT/EP2014/051670.

$^1$H-NMR analysis on the -DAB derivatives were conducted as above reported for Example 1.

The schemem set forth in the Figure, represents the general LPS structure of Enterobacteriaceae with the located sites of DAB-activation (necessary for conjugation to the carrier protein) and the necessary biological detoxification, preferentially performed by SAEP (Synthetic Anti Endotoxin Peptide), which allows to achieve detoxification while LPS retaining its supramolecular, micelle-like, antigenic structure).

Derivatization of LPS of S. enteritidis, S. paratyphi a and S. dysenteriae to their Homologous Active Esters as LPS-DAB-MSE Derivatives This step has been performed according to the process disclosed by the applicant in Claim 8 of the European Patent EP 1501542.

Simultaneous Coupling of the Three Activated (Poly-Functional) LPS to the (Poly-Functional) Carrier Protein Enterotoxoid A The chemical equation reported above in Example 1, also applies to the conjugates of Toxoids and LPS-derivatives:

$$\text{Toxoid}+4\ \text{LPS-DAB(MSE)}\rightarrow\text{Toxoid-(LPS)}_3+\text{LPS-DAB(MSE)}$$

So that:

$$Keq=\frac{[Toxoid\text{-}(LPS)_3][LPS\text{-}DAB(MSE)]}{[Toxoid][LPS\text{-}DAB(MSE)]^4}=\frac{[Toxoid\text{-}(LPS)_3]}{[Toxoid][LPS\text{-}DAB(MSE)]^3}$$

The equation refers to the concentration of the total active esters (MSE) deriving from the sum of equal parts of the DAB-activated LPS antigens, which are in turn comparable to the amount of the DAB linker quantitated by $^1$H-NMR spectrometry which is present in each activated LPS antigen (conversion rate of Ps-DAB to Ps-DAB(MSE) ≥98% on molar basis).

The chemical synthesis of the conjugate, also known as coupling reaction, has been performed according to the process disclosed by the applicant in Claim 8 of the European Patent EP1501542. The procedure, however, can be here considered as innovative because the three coupling reactions are simultaneously run, rather than proceeding in one coupling reaction at the time (or step-by-step process). This procedure may be preferred to the step-by-step coupling of each Ps-activated antigen for the simple reason of shorting the reaction time, therefore improving the efficiency of the reaction, provided that the three activated-Ps are in the condition to comparatively compete at the equilibrium for the coupling reaction (this feature include comparable average MW, comparable range of LPS-DAB activation and comparable stoichiometric ratios among the reacting groups of the protein and those of the activated LPS). The molecular constructs obtained in this way, however, result to be toxic because the Lipid A moiety of LPS is actively present in the molecular structure. In order to pursue and achieve the safe use of the Toxoid-LPS conjugate entity, the LPS structure must therefore undergo detoxification alternatively through cleaving out the Lipid A moiety, or by saturation of the Lipid A-binding site through a specific strategy that use the Synthetic Anti-Endotoxin Peptides (SAEP). The latter is the preferred embodiment in the context of the present invention (see next example 3).

Example 3: Preparation of Enterotoxoid A-Endotoxoid Conjugates and Cytotoxoid B-Endotoxoid Conjugates from their Homologous Enterotoxoid A-LPS (Endotoxin)/Cytotoxoid B-LPS (Endotoxin) Conjugates Endotoxoids are non-toxic antigens able to induce specific immunological activity against their homologous LPS which are the native main toxic antigens exposed on the surface of the Gram (−) bacteria.

A comprehensive, publically available, textbook which is exhaustive on the many scientific aspects of Endotoxin antigens originating from Gram-negative bacteria is "Endotoxins" by Kevin L. Williams, Editor, Informa Health Care USA Inc., publisher, New York (2007).

An Endotoxoid is a molecular entity composed of an equimolar complex of SAEP, Synthetic Anti Endotoxin Peptides, with the Lipid A moiety of LPS (Endotoxin):

$$\text{Toxoid-(LPS)}_3+3\ \text{SAEP}\rightarrow\text{Toxoid-(Endotoxoid)}_3$$

An Endotoxoid, originating from a given species-specific (immunotype), Endotoxin (Lipopolysaccharide), is prepared according to the scientific concept reported by Rustici et al. (Science 259: 361-365, 1993) and in the previously disclosed molecular details reported in the U.S. Pat. No. 6,951,652 and in the U.S. Pat. No. 7,507,718.

The immunological activity of an Endotoxoid involves polyclonal antibodies of the IgG (mainly) and IgM isotypes having biological activity (bactericidal effect) via the mechanism known in immunology as Opsonophagocytosis (OP, or antibody-mediated engulfing of bacteria in macrophages and PMC) and Direct Bactericidal (DB, antibody-mediated lysis of the bacterial cell wall), both mechanisms being mediated by activation of the complement pathway.

Endotoxoids are helper-T dependent antigens in animal models but not yet experienced in human infants, where the immune system is not fully developed until an age over 2 years. For this reason, the conjugation to helper-T dependent carrier proteins like the two above reported protein Toxoids of *C. difficile* has been considered in the present Application for preparing the desired vaccine product.

Accordingly, the conjugates of Enterotoxoid A or Cytotoxoid B with selected species-specific LPS (Endotoxin) have been reacted with SAEP2 (Rustici et al., Science 259: 361-365, 1993) in the conditions generally reported in the U.S. Pat. No. 7,507,718 (see pages 33-34 and Claim 17), in order to achieve the detoxification of the Toxoid-conjugated LPS so that the relative homologous Toxoid-conjugated Endotoxoids are formed.

The following Toxoid-conjugated Endotoxoids have been prepared:

Enterotoxoid A covalently conjugated to Endotoxoids of *S. paratyphi* A, *S. dysenteriae, S. enteritidis;*

Cytotoxoid B covalently conjugated to Endotoxoids of *S. paratyphi* A, *S. dysenteriae, S. enteritidis;*

CRM197 covalently conjugated to Endotoxoids of *S. paratyphi* A, *S. dysenteriae, S. enteritidis* as a well established helper-T dependent carrier protein useful in controlling the immunization experiments in animal models.

Example 4: Combination of the Tetravalent Conjugate Antigen Comprising Polysaccharides of S. typhi (Vi), E. coli (K1) and V. cholerae (O139) Conjugated to the Carrier Protein Enterotoxoid A, with the Tetravalent Conjugate Antigen Comprising LPS/Endotoxoids of *S. enteritidis, S. paratyphi* A and *S. dysenteriae* Conjugated to the Carrier Protein Cytotoxoid B The combination is prepared by associating the two kind of molecular models at the dose as appropriate for immunogenic studies in animal models below reported in the Example 8.

Example 5: Physical-Chemical Analysis of the Antigenic Multivalent Molecular Construct Comprising the Polysaccharides of *S. typhi* (Vi), *E. coli* (K1) and *V. cholerae* (0139) Conjugated to the Carrier Protein Enterotoxoid A or Cytotoxoid B The GPC analysis (Gel Permeation Chromatography) on Sepharose 4B-CL has been used to perform the physical analysis of the antigenic multivalent molecular construct of Example 1. Purification of the High Molecular Weight (HMW)-multivalent antigen is simply obtained by collecting and pooling the eluted fractions from Kd=0.00 to Kd=0.30.

Polymers of the basic unit of the molecular construct are obtained as cross-linked molecular entities because of the polyfunctionality of the Ps antigens (about 2% of DAB activation, on molar basis, as evidenced by $^1$H-NMR spectroscopy) and the polyfunctionality of the carrier protein (ca. 104 reactive amino groups/mole Toxoid A, as determined by TNBS reaction, remaining from the native 223 Lys residues of the Toxin A +1 amino terminal AA, within the structure encompassing the whole 2,710 AA of the sequence; ca. 85 reactive amino groups/mole Toxoid B, as determined by TNBS reaction, remaining from the native 156 Lys residues of the Toxin B+1 amino terminal AA, within the structure encompassing the whole 2,366 AA of the sequence).

In light of the above, the conjugate under analysis appears as a polydispersed, monomeric to polymeric, molecular entity which contains the basic unit of the molecular construct reported in the chemical equation, with a HMW which derives from the basic polymerized unit encompassing the Enterotoxoid A ($MW=3.08\times10^5$) or Cytotoxoid B ($MW=2.70\times10^5$) and an average of $MW=10^5$ for each of the three Ps/LPS antigens (or a total of ca. $3.0\times10^5$) resulting in a comprehensive average MW of $6.10\times10^5$ per basic unit; accordingly, the several cross-linked units of such basic structure is reaching several millions and are mainly eluted at the Vo of the Sepharose 4B-CL column.

The w/w ratio between the carrier protein and each of the three type-specific Ps is ca. 3.6 (Table 1, below); this w/w ratio yields an average molar ratio (R) protein/type-specific Ps of ca. 1.0, corresponding to an average ratio of one mole of protein/mole of type-specific Ps, as well suggested by the chemical equation. Accordingly, the experimentally obtained, cross-linked, molecular entity responds to a molecular model constituted by several polymeric units of the basic unit just consisting of one mole of carrier protein carrying a total of three moles of type-specific Ps (one mole for each type-specific Ps).

Example 6: Immunochemical Analysis of the Antigenic Multivalent Molecular Construct Enterotoxoid A-PsVi, PsK1, Ps0139 or Cytotoxoid B-PsVi, PsK1, Ps0139

The GPC purified molecular construct was analyzed by inhibition-ELISA for determining the serological specificity of the four serum different polyclonal antibodies (PAbs) and for determining the qualitative and quantitative presence of each antigen of the construct, as disclosed in the international patent application PCT/EP2014/051670.

The comparison between chemical titration and immunochemical titration of carbohydrate antigens for testing their quantitative equivalence, was performed by the use of inhibition-ELISA, through the experimentally determined parameter $MIC_{50}$ (Minimal Inhibitory Concentration of the selected carbohydrate antigen working as inhibitor of the homologous reference Ps-Ab reaction) in order to evaluate and correlate accuracy and precision of the immunochemical method with respect to the chemical one in the analytical control of such a kind of molecular construct.

Example 7: Determination of the Concentration for the Carbohydrate Antigen in Either Activated or Multivalent Conjugated Form: Comparison of Chemical Titration Vs. Immunochemical Titration Immunochemical titers are obtained according to the method reported above relative to the Inhibition-ELISA as compared to chemical titers obtained according to the methods reported in the specific sections of the international patent application PCT/EP2014/051670; immunochemical titers of unknown samples of each of the three carbohydrate-specific antigens, either in activated or conjugated form, were determined by interpolation on the linear part of a reference standard curve built by inhibition-ELISA using known, chemically titred, carbohydrate antigen amount.

The same methodology described for the qualitative and quantitative immunochemical analysis of each molecular construct above reported, is then used for characterization of the final formulation of the polyvalent vaccine containing the association of the two molecular constructs, each constituted by a triad of Ps/LPS (Endotoxoid) conjugates of the two Toxoids of *C. difficile* used as carrier proteins, in order to get the complete characterization of an exemplificative 4-valent or 8-valent vaccine.

Example 8: Vaccine Formulation as Related to the Stoichiometry of the Multi-Valent Molecular Constructs Such kind of broad-spectrum formulations for an Enteric Vaccine can be safely prepared by the use of molecular constructs of the present invention, which allows a reduced use of protein carrier for carrying such a number of conjugated Ps and LPS (Endotoxoids) antigens. As specifically referred to an exemplified formulation of an Enteric Vaccine containing an 8-valent formulation which includes the most prevalent, epidemiologically significant, specific Ps and LPS/(Endotoxoids), the following molecular constructs (Table 1) have been synthesized and analyzed as an extended exemplification of the preferred embodiments, according to the methods reported above in the various Examples detailing the molecular constructs based on Enterotoxoid A and Cytotoxoid B carrying Ps/LPS (Endotoxoids), as well as the combination of the two.

The total amount of the two carrier protein Toxoids exemplified in this 8-valent Enteric Vaccine prepared and formulated according to the procedures reported in this application and defined by the stoichiometry of the resulting molecular constructs, each one expressing built-in multiple epitopes, is coherent with the following molar composition relatively to the dose of each molecular construct containing ca. 1 ug of each of the two carrier protein Toxoids (MW=308K and 270K, respectively) and ca. 0.3 μg of each of the three selected DAB-activated, type-specific, Ps/LPS (Endotoxoid) antigens (average MW=100K based on two different criteria of analysis, that is estimating the average sizing by molecular filtration on calibrated filter membranes and estimating sizing by GPC, in all cases using reference carbohydrate molecules like Dextrans of various MW).

TABLE 1

| Molecular Construct | Average weight ratio Toxoid/Ps | Average molar ratio Toxoid/Ps |
|---|---|---|
| EnteroTox A for: | | |
| $Ps_{E.\ coli}$ | 3.30 | 1.08 |
| $Ps_{S.\ typhi}$ | 3.80 | 1.24 |
| $Ps_{V.\ cholerae}$ | 4.05 | 1.33 |
| CytoTox B for: | | |
| $EndoTox_{S.\ enteritidis}$ | 3.65 | 1.36 |
| $EndoTox_{S.\ paratyphi\ A}$ | 3.01 | 1.12 |
| $EndoTox_{S.\ dysenteriae}$ | 3.90 | 1.45 |

In the exemplified molecular constructs, the mean of the (w/w) ratio Protein to Ps/LPS is: 3.61±0.39 (10.8%) corresponding to the mean of the (mol/mol) ratio: 1.26±0.14 (11.1%).

The concept of calculating and comparing the features of conjugate antigens on molar basis is fundamental because the immune system processes antigens on molar basis, as Nature does in each chemical or biochemical reaction of transforming matter, therefore referring to the antigen's MW.

Accordingly, depending from the average MW of each type-specific Ps/LPS antigen and that of the protein carrier Toxoids, the molar ratios of conjugate antigens are subject to change by the selection of their antigen components. It is mostly preferred that molar ratios between carrier protein and each type-specific Ps antigen be equal to or higher than 1.0 for a likely optimal expression of helper T-dependency. In addition to this molar parameter, it is also important considering the average amount of covalent bonds interposed between the protein and each type-specific carbohydrate antigen, which parallels the activation rate of the type-specific polysaccharide, since this hybrid molecular region is the one experimentally suggested as responsible for the acquired helper T-dependent properties of a conjugate molecule (Arndt and Porro, 1991).

It is however possible to synthesize the molecular constructs according to different stoichiometries of synthesis, as detailed in the international patent application PCT/EP2014/051670, by addressing the amount of reagents participating to the chemical equilibrium reported in the above chemical equation, which may lead to a molecular construct of different stoichiometry, where the amount of helper T-dependent carrier protein in the molecular construct can be optimally selected according to the optimal expression of immunogenicity of such molecular construct in the various age groups of the human population. In both, above exemplified, 4-valent to 8-valent formulations, containing one to two molecular constructs each carrying three type-specific Ps/LPS, the total amount of each carrier protein Toxoid is ca. 1 μg, while the conjugated type-specific Ps/LPS (Endotoxoid) are in the amount of ca. 0.3 μg, respectively.

Accordingly, it is the purpose of the above reported embodiments to provide evidence of the fact that the disclosed multivalent antigenic molecular construct with built-in epitopes can be synthesized in a broad range of stoichiometric parameters in order to then properly define, in mammalian hosts and particularly in humans, the optimal dose of the construct even when considering the different age-groups (from infants to elders) to be immunized by such a broad-spectrum vaccine formulation.

Table 2 below, shows different molecular models obtained for the above concept, by making use of the same chemical reaction of synthesis, although using different "ad hoc" chosen stoichiometries for the reagents participating to the equilibrium.

Here below, are reported some considerations on the two Toxoids used in the present application, Enterotoxoid A and Cytotoxoid B, since they are (or may be) chemically-treated derivatives of the homologous Toxins. This historic procedure, used for historic vaccines like Tetanus Toxoid and Diphtheria Toxoid, is necessary for having the Toxins purposely detoxified for a safe human use as immunogens. In the present Application, we have considered the average MW of the purified Toxoids as being comparable to that of the Toxins from which they derive.

However, among other features, the marked difference between Toxoids and Toxins resides in the amount of residual primary amino groups from the Lysine residues which remain in the Toxoid structures after the chemical detoxification. An average of 47% to 54% reactive amino groups are about to be detected in the Toxoids with respect to those originally present in the structure of the homologous Toxins, which work as nucleophylic groups in the coupling reaction with the activated Ps/LPS antigens. When comparing the structure of the two Toxoids to that of a consolidated, historic, carrier protein like CRM197, in terms of capability to compete in the coupling reaction as nucleophylic reagent, one may determine that Toxoid A has ca. 104 amino groups/mole (MW=$3.08\times10^5$ for 2,710 AA) while Toxoid B has ca. 85 amino groups/mole (MW=$2.7\times10^5$ for 2,366 AA), so that the molar density of them (which we define as "molar nucleophile activity") is 3.84% in Enterotoxoid A and 3.60% in Cytotoxoid B, two parameters that are significantly lower than that calculated for CRM197 (7.47%) which does have a higher capability to serve as nucleophylic reagent in a given coupling reaction (as detailed in the international patent application No. PCT/EP2014/051670). However, given the significant difference in the MW of the two protein Toxoids (basically a factor=5.3 and 4.7 in their favor with respect to CRM197) the molar ratios of the protein carrier, for each of the carried carbohydrate antigens selected in the molecular constructs, may result advantageous for the Toxoids when one is willing to limit the amount of carrier protein/dose in a polyvalent formulation. In fact, at comparable weight doses of the two carrier protein Toxoids, they result to be about 5.0 times lower than CRM197 on molar basis. Accordingly, attention must be paid to the fact that the carrier MW is an important parameter affecting the physical-chemical features of the conjugates and may limit the possibility to obtain a molar ratio Toxoid/specific Ps/LPS with a value ≥1.0 for the optimal induction of T-helper dependency in the host's immune system. Table 2 lists all the molecular models synthesized for the work detailed in the present Application, representative of the various stoichiometries used for the purpose, which are dependent from: i) the MW of the carrier protein used; ii) the molar nucleophile activity of such carrier proteins (expressing the amount of —$NH_2$ groups/mole of protein); iii) the average MW of the activated Ps/LPS antigens and, iv) the respective activation rate of the Ps/LPS antigens (DAB-MSE groups for then reacting with the —$NH_2$ groups of the protein). The exemplified molecular models make evidence for the flexibility of the chemistry adopted and the fact that the carrier protein may be present in the conjugate entity in a broad variety of ponderal and molar ratios, above 1.0 and below 1.0. In particular, the molar ratio Protein/Ps ranged from at least 0.3 to 1.0 when considering each type-specific or group-specific Ps present in the glycoconjugate, and from at least 0.3 to 1.0 when considering the total of the three Ps, each Ps contributing for about one third to the total amount finally present in the glycoconjugate.

TABLE 2

| Molecular Construct | Average weight ratio Toxoid/Ps | Average molar ratio Toxoid/Ps |
|---|---|---|
| EnteroTox A for: | | |
| $Ps_{E.\,coli}$ | 3.30 | 1.08 |
| $Ps_{S.\,typhi}$ | 3.80 | 1.24 |
| $Ps_{V.\,cholerae}$ | 4.05 | 1.33 |
| $Ps_{E.\,coli}$ | 1.05 | 0.34 |
| $Ps_{S.\,typhi}$ | 1.15 | 0.37 |
| $Ps_{V.\,cholerae}$ | 1.03 | 0.33 |
| $EndoTox_{S.\,enteritidis}$ | 3.35 | 1.09 |
| $EndoTox_{S.\,paratyphi\,A}$ | 3.00 | 0.97 |
| $EndoTox_{S.\,dysenteriae}$ | 3.20 | 1.04 |
| $EndoTox_{S.\,enteritidis}$ | 1.13 | 0.37 |
| $EndoTox_{S.\,paratyphi\,A}$ | 1.20 | 0.39 |
| $EndoTox_{S.\,dysenteriae}$ | 1.05 | 0.34 |
| CytoTox B for: | | |
| $EndoTox_{S.\,enteritidis}$ | 3.65 | 1.36 |
| $EndoTox_{S.\,paratyphi\,A}$ | 3.01 | 1.12 |
| $EndoTox_{S.\,dysenteriae}$ | 3.90 | 1.45 |
| $EndoTox_{S.\,enteritidis}$ | 1.23 | 0.46 |
| $EndoTox_{S.\,paratyphi\,A}$ | 1.02 | 0.38 |
| $EndoTox_{S.\,dysenteriae}$ | 1.15 | 0.43 |
| $Ps_{E.\,coli}$ | 3.60 | 1.33 |
| $Ps_{S.\,typhi}$ | 3.45 | 1.28 |
| $Ps_{V.\,cholerae}$ | 3.85 | 1.43 |
| $Ps_{E.\,coli}$ | 1.25 | 0.46 |
| $Ps_{S.\,typhi}$ | 1.10 | 0.40 |
| $Ps_{V.\,cholerae}$ | 1.43 | 0.53 |

Example 9: Immunological Analysis in Animal Models of the Antigenic Multivalent Molecular Constructs of Enterotoxoid a and Cytotoxoid B (Originating from the Homologous Toxins of *C. difficile*) Carrying Polysaccharides (*S. typhi, V. cholerae, E. coli*) or LPS/Endotoxoids (*S. paratyphi A, S. dysenteriae, S. enteritidis*)

The two kind of conjugates using the two protein Toxoids from *C. difficile*, have been experienced in a murine animal model for active immunization experiments. As helper-T dependent control immunogen, the homologous conjugates of CRM197 were used in parallel experiments.

Vaccine Formulation for Ps-Conjugates

Enterotoxoid A and Cytotoxoid B conjugates of PsVi, Ps0139 and PsK1 were combined. Stoichiometric features of the conjugates showed a mean ratio Protein/each of the type-specific Ps of 3.61±0.39 (w/w) as shown in Table 1, above.

Vaccine Formulation for LPS/Endotoxoids-Conjugates

Enterotoxoid A and Cytotoxoid B conjugates of LPS *S. enteritidis, S. dysenteriae* and *S. paratyphi A* were combined. Stoichiometric features of the conjugates showed a mean ratio Protein/each of the type-specific LPS/Endotoxoid of 3.61±0.39 (w/w) as shown in Table 1, above.

Combined Broad-Spectrum Enteric Vaccine Formulation for Ps-Conjugates and LPS (Endotoxoids)-Conjugates Using the Carrier Proteins Enterotoxoid A and Cytotoxoid B Enterotoxoid A conjugates of PsVi, Ps0139 and PsK1 and Cytotoxoid B conjugates of LPS (Endotoxoids)*S. enteritidis, S. dysenteriae* and *S. paratyphi A* were combined for the purpose.

Dose and Formulations of the Exemplary Vaccines

According to the stoichiometry of the molecular constructs reported above in Table 1, the injected dose is ca. 1.0 µg for each Ps/LPS (Endotoxoid) conjugated present in each molecular construct and for each Toxoid (ca. 3.0 µg) contained in the Vaccine Formulation; the dose becomes ca. 6.0 µg of total protein amount when the Vaccine Formulation contains the combined Toxoids for the same or different triads of carried Ps/LPS (Endotoxoid) antigens (Broad-spectrum Vaccine); $AlPO_4$ is used as adjuvant at the fixed dose of 0.5 mg/dose (equivalent to ca. 0.120 mg of Alum). Adsorption of each multivalent molecular construct to the mineral adjuvant occurred at ≥80%, on weight basis, as estimated by inhibition-ELISA.

Animals

Each group of animals selected for each of the below reported immunization experiments, contained 10 female Balb/c mice.

Route i. p.

Immunization Schedule 0, 2, 4 weeks; bleeding at week 0, 2, 4, 6.

Control immunization with plain Ps antigens were omitted on the basis of the historical knowledge that highly purified Ps antigens are not significantly immunogenic in mammalians and do not "boost" IgG isotype antibodies following repeated injections of it.

ELISA Titers

Titers expressed as end-point reaction showing O.D. ≥2.0 relative to the control reactions for each type-specific Ps/LPS (Endotoxoid) and the two protein Toxoids. Sera pool dilutions are performed serially, in twofold fashion, starting from dilution 1/200.

Immunological Results

Geometric Mean Titers of IgG to specific Ps/LPS (Endotoxoid) or to each of the two Toxoids, in murine sera pool, as determined by ELISA. SD is within ±25% of the reported Geometric Mean. Unless otherwise indicated, the statistical significance among sera titers (determined by t-test) was <0.01. Results are summarized in the following Table 3 and 4.

In Vitro Neutralization of the Homologous Toxins

Performed as reported by Porro et al. (1980) for Diphtheria Toxin and as Pavliakova et al. (2000) for *C. difficile* Toxins.

Table 3 illustrates the immunoresponse of mice to the molecular model involving Enterotoxoid A and Cytotoxoid B as carrier protein for Ps antigens of *E. coli, V. cholerae, S. typhi*.

TABLE 3

|  | Enterotoxoid A | | | | Cytotoxoid B | | | |
| --- | --- | --- | --- | --- | --- | --- | --- | --- |
| Ps | W0 | W2 | W4 | W6 | W0 | W2 | W4 | W6 |
| Vi | <200 | 200 | 2,600 | 15,800 | <200 | 200 | 2,200 | 18,900 |
| K1 | <200 | 200 | 3,200 | 12,400 | <200 | 200 | 2,400 | 20,000 |
| 0139 | <200 | 200 | 1,800 | 11,600 | <200 | 200 | 1,200 | 14,800 |
| Tox | <200 | 2,800 | 25,800 | 84,400 | <200 | 3,200 | 32,600 | 95,400 |

Table 4 shows the immunoresponse of mice to the molecular model involving Enterotoxoid A and Cytotoxoid B as carrier for LPS/Endotoxoids antigens of *S. enteritidis*, *S. paratyphi* A, *S. dysenteriae*.

TABLE 4

|  | Enterotoxoid A | | | | Cytotoxoid B | | | |
| --- | --- | --- | --- | --- | --- | --- | --- | --- |
| LPS(Endotoxoid) | W0 | W2 | W4 | W6 | W0 | W2 | W4 | W6 |
| S. enteritidis | <200 | 400 | 3,600 | 12,800 | <200 | 200 | 1,800 | 10,400 |
| S. paratyphi A | <200 | 200 | 2,400 | 14,800 | <200 | 400 | 3,600 | 16,400 |
| S. dysenteriae | <200 | 200 | 2,200 | 16,400 | <200 | 400 | 2,800 | 14,200 |
| Toxoid | <200 | 3,400 | 28,200 | 66,400 | <200 | 2,400 | 24,800 | 84,200 |

The results depicted in the above Tables 3 and 4 show the anamnestic induction of biologically functional IgG isotype antibodies for each of the four components of the two multivalent molecular constructs (Toxoid-Ps and Toxoid-Endotoxoid multivalent conjugates).

Particularly, any boosting activity on the immune system observed for the carrier protein is in parallel observed for each of the carried Ps antigens, typical and well known behavior of helper T-dependent antigens. The booster effect obtained against the two Toxoids and the biological activity of the induced anti-Toxoid antibodies also strongly supports the fact that the multivalent molecular construct has the potential to work as antigen in humans for the prevention of toxicity due to the homologous Toxins. The following results were collected, expressed as fold-increase in respect to pre-immunization titers, of the sera GMT obtained following the second booster dose and reported in the following Table 5 as anti-toxic titers.

TABLE 5

| Toxoid | Abs to homologous Toxin (fold increase for toxin neutralization, in vitro) |
| --- | --- |
| Enterotoxoid A | 456 |
| Cytotoxoid B | 562 |
| CRM197 | 824 |

The above detailed results, although just focusing on some specific examples, support the preparation and use of a broad-spectrum enteric vaccine for inducing immunity in a mammalian host against the carrier proteins Enterotoxoid A and Cytotoxoid B of *C. difficile* as well as against the carried Ps of *E. coli*, *V. cholerae*, *S. typhi* and the carried Endotoxoids of *S. paratyphi* A, *S. dysenteriae*, *S. enteritidis*. Based on the above, the capsular Ps of *C. difficile* may be also considered as Ps antigens carried by the two Toxoids of the homologous pathogen, according to the detailed molecular construct.

The formulation of a broad-spectrum vaccine as the one above reported in Examples 8 and 9, has objective advantages on a vaccine formulation which considers the simple and eventual association of each of the six different Ps/LPS (Endotoxoid) conjugates of each of the two Toxoid proteins:

A) by using the molecular model with built-in multiple-epitopes one may actually reduce the amount of carrier protein present in the broad-spectrum formulation (e.g.: the use of just two triads of conjugates does reduce the amount of protein carrier to ⅓ or 33% of the amount of carrier protein present in the associated formulation of the six conjugates);

B) the number of injections would be reduced to a total of 3 injections with an obvious saving of materials and resources in addition to the lower stress of the mammalian host involved (a minimum of 3 injections, one priming dose and two booster doses, for each of the six individual type-specific vaccines, would result in a total of 18 injections).

BIBLIOGRAPHY

Arndt and Porro, Immunobiology of Proteins and Peptides, Edited by M. Z. Atassi, Plenum Press, New York and London, pages 129-148, 1991.
Chan M. eta al. Scientific reports (www.nature.com), DOI 10.1038/srep11507 of Jun. 17, 2015.
Dagan R. et al. Vaccine, 28:5513-5523 (2010)
Donald R. et al. Microbiology, 159: 1254-1266, 2013.
Endotoxins. Kevin L. Williams, Editor, Informa Health Care USA Inc., publisher, New York, 2007.
European patent EP 1,501,542.
U.S. Pat. No. 6,951,652.
U.S. Pat. No. 7,507,718.
Jones M. K. et al., Science, 346: 755-759, 2014.
Lee L. H. and Blake M. S., Clinical and Vaccine Immunol., pg. 551-556 (2012)
Libby J. M. et al., Infect. Immun. 36: 822-829, 1982.
Lindesmith L C et al. (2015), PLoS Med 12 (3): e1001807. doi:10.1371/journal.pmed.1001807
Liverly D. M. et al., Infect. Immun. 47:349-352, 1985.
Lowy I. et al., New England J. Med. 362: 197-205, 2010.
Pavliakova D. et al., Infect. Immun., 68:2161-2166, 2000.
International patent application WO2004/052394 A1.
International patent application No. PCT/EP2014/051670.
Porro M. et al. Molecular Immunology, 23: 385-391, 1986.

Porro M. et al. J. Infect. Dis., 142:716-724,1980
Romano M. et al., Toxins, 6:1385-1396, 2014.
Rupnick M. et al. Nat Rev Microbiol. 7(7):526-536, 2009.
Rustici A. et al., Science 259: 361-365, 1993.
Salcedo J. et al., Gut, 41:366-370-1997.
Simor A. E. et al. Infection Control and Hospital Epidemiology, Vol. 23, No. 11,696-703, 2002.
Sougioultzis S. et al., Gastroenterology, 128: 764 770, 2005.

The invention claimed is:

1. A method for the protection of a subject from systemic and enteric infections due to at least one of the enteropathogenic bacteria selected among *Clostridium difficile, Salmonella typhi, Escherichia coli, Vibrio cholerae, Salmonella enteritidis, Shigella flexneri, Shigella sonnei, Salmonella paratyphi A, Salmonella dysenteriae, Salmonella cholerasuis, Klebsiella, Enterobacter* or a combination thereof, said method comprising administering an effective amount of a vaccine comprising an antigenic multivalent molecular construct consisting of basic units comprising the helper-T dependent carrier detoxified proteins selected between Enterotoxoid A and Cytotoxoid B from *Clostridium difficile* covalently bound to a minimum of three carbohydrate structures from enteropathogenic bacteria selected between bacterial polysaccharides or detoxified lipopolysaccharides of different serological specificity, wherein each carbohydrate structure comprises at least one of the repeating basic epitopes consisting of a minimum of five to twelve monosaccharide residues, wherein at least one mole of carrier protein is bound to at least one mole of each of the at least three carbohydrate structure or their molar sum to form carried carbohydrate structures of different serological specificity in a physiologically acceptable vehicle, optionally together with a pharmaceutically acceptable adjuvant or excipient.

2. A method for the protection of a subject from systemic and enteric infections due to at least one of the enteropathogenic bacteria according to claim 1 where said subject is a human.

* * * * *